United States Patent
Talalay et al.

(10) Patent No.: US 9,585,894 B2
(45) Date of Patent: Mar. 7, 2017

(54) COMPOSITIONS COMPRISING EXEMESTANE AND NOVEL METHODS OF USE

(71) Applicant: THE JOHNS HOPKINS UNIVERSITY, Baltimore, MD (US)

(72) Inventors: Paul Talalay, Baltimore, MD (US); Hua Liu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/333,914

(22) Filed: Jul. 17, 2014

(65) Prior Publication Data

US 2015/0025049 A1    Jan. 22, 2015

Related U.S. Application Data

(60) Provisional application No. 61/856,242, filed on Jul. 19, 2013, provisional application No. 61/892,545, filed on Oct. 18, 2013.

(51) Int. Cl.

| | |
|---|---|
| *A61K 31/352* | (2006.01) |
| *A61K 31/5685* | (2006.01) |
| *A61K 31/26* | (2006.01) |
| *A61K 31/05* | (2006.01) |
| *A61K 31/122* | (2006.01) |
| *A61K 31/353* | (2006.01) |
| *A61K 31/165* | (2006.01) |
| *A61K 31/12* | (2006.01) |

(52) U.S. Cl.
CPC .......... *A61K 31/5685* (2013.01); *A61K 31/05* (2013.01); *A61K 31/12* (2013.01); *A61K 31/122* (2013.01); *A61K 31/165* (2013.01); *A61K 31/26* (2013.01); *A61K 31/352* (2013.01); *A61K 31/353* (2013.01)

(58) Field of Classification Search
CPC .... A61K 31/12; A61K 31/165; A61K 31/122; A61K 31/26; A61K 31/05; A61K 31/352; A61K 31/353; A61K 31/5685; A61K 31/121

See application file for complete search history.

(56) References Cited

U.S. PATENT DOCUMENTS

| | | |
|---|---|---|
| 7,846,918 B2 | 12/2010 | Pariza et al. |
| 2014/0271923 A1 * | 9/2014 | Reid .............................. 424/651 |

FOREIGN PATENT DOCUMENTS

| | | |
|---|---|---|
| WO | 2007130353 A2 | 11/2007 |
| WO | WO 2009108361 A1 * | 9/2009 |
| WO | WO 2011131314 A1 * | 10/2011 |

OTHER PUBLICATIONS

Carlsen, H., et al., "In vivo imaging of NF-KB activity" The Journal of Immunology (2002) vol. 168, pp. 1441-1446.
Fahey, J., et al., "The chemical diversity and distribution of glucosinolates and isothiocyanates among plants" Phytochemistry (2001) vol. 56, pp. 5-51.
Fahey, J., et al., "The prochaska microtiter plate bioassay for inducers of NQO1" Methods in Enzymology (2004) vol. 382, pp. 243-258.
Liu, H., et al., "Relevance of anti-inflammatory and antioxidant activities of exemestane and synergism with sulforaphane for disease prevention" PNAS (2013) vol. 110, No. 47, pp. 19065-19070.
Mauras, N., et al., "Pharmacokinetics and dose finding of a potent aromatase inhibitor, aromasin (exemestane), in young males" The Journal of Clinical Endocrinology & Metabolism (2003) vol. 88, No. 12, pp. 5951-5956.
Pezzuto, J., et al., "Characterization of natural product chemopreventive agents", Cancer Chemoprevention 2 (pp. 3-37). Strategies for Cancer Chemoprevention. GJ Kelloff, ET Hawk, CC Sigman (eds.), Humana Press, Totowa, NJ (2005).
Ramos-Gomez, M., et al., "Sensitivity to carcinogenesis is increased and chemoprotective efficacy of enzyme inducers is lost in nrf2 transcription factor-deficient mice" PNAS (2001) vol. 98, No. 6, pp. 3410-3415.
Suh, N., et al., "Novel triterpenoids suppress inducible nitric oxide synthase (iNOS) and inducible cyclooxygenase (COX-2) in mouse macrophages" Cancer Research (1998) vol. 58, pp. 717-723.
Goss, P., et al., "Exemestane for breast-cancer prevention in postmenopausal women" N. Engl. J. Med. (2011) vol. 364, No. 25, pp. 2381-2391.
Amaral, C., et al., "Apoptosis and autophagy in breast cancer cells following exemestane treatment" PLoS ONE, vol. 7, No. 8, e42398, (Aug. 2012).
Gamet-Payrastre, L., et al., "Sulforaphane, a naturally occurring isothiocyanate, induces cell cycle arrest and apoptosis in HT29 human colon cancer cells" Cancer Research (2000) vol. 60, pp. 1426-1433.
International Search Report and Written Opinion dated Nov. 12, 2014 in related PCT application filed Jul. 17, 2014.

* cited by examiner

*Primary Examiner* — Titilayo Moloye
(74) *Attorney, Agent, or Firm* — John Hopkins Technology Transfer

(57) ABSTRACT

In addition to its potent mechanism-dependent inhibition of estrogen biosynthesis, in accordance with the embodiments of the present invention, it has now been found that exemestane has novel chemoprotective properties which have hitherto not been explicitly recognized. The present invention provides methods for the use of compositions comprising exemestane for chemoprotection against a wide variety of non-mammary tumors (and possibly other chronic diseases) that are not estrogen-dependent, but have oxidative stress, inflammation and electrophile-damaging etiologies. The present invention also shows that exemestane shows powerful synergism with other classes of Nrf2-activators and phase 2 enzyme gene activators, including, for example sulforaphane (an isothiocyanate), shikonin (a naphthoquinone), zerumbone (a cyclic sesquiterpene) and resveratrol (a stilbene derivative), which increases the attractiveness of exemestane's novel uses.

3 Claims, 9 Drawing Sheets

COMPOSITIONS COMPRISING EXEMESTANE AND NOVEL METHODS OF USE

REFERENCE TO RELATED APPLICATIONS

This application claims the benefit of U.S. Provisional Patent Application Nos. 61/856,242, filed on Jul. 19, 2013, and 61/892,545, filed on Oct. 18, 2013, both of which are hereby incorporated by reference for all purposes as if fully set forth herein.

BACKGROUND OF THE INVENTION

Development of safe and effective agents for reducing the risk of cancer and other chronic diseases is a high priority of contemporary medicine. Implementation of strategies for chemoprevention/chemoprotection is beset with many problems.

In the economically developed world, the mammary gland is the most common target of malignancy in women. Thus, in the U.S. alone, 232,340 new diagnoses and 39,620 deaths of women from breast cancer were projected for 2013, and the global burden of new cases is enormous. The majority of breast malignancies are estrogen receptor-positive at the time of diagnosis and their growth is under estrogen control: thus this process is an effective target for both prevention and treatment of breast cancer by two mechanisms: (i) selective modification of estrogen binding to their receptors exemplified by such widely used agents as tamoxifen and raloxifene, and (ii) blocking of estrogen biosynthesis by inhibition of its final and rate-limiting step, the aromatase reaction, by steroidal compounds such as exemestane and nonsteroidal letrozole and anastrozole. Both these approaches have been highly successful, and multiple clinical studies attest to their benefits. Thus, a recent study of 4560 women at moderately increased risk for developing breast cancer showed that exemestane reduced the risk of breast cancer by 65% relative to placebo. Exemestane has been administered to women with breast cancer in combination with tamoxifen or with cyclooxygenase inhibitors, without increased adverse effects.

Albeit exemestrane has been tested in males, it is considered generally as an aromatase inhibitor. Mauras, N. et al., J. Clin. Endocrin. Metab. 88(12):5951-5956 (2003).

SUMMARY OF THE INVENTION

The chemical structure of exemestane (6-methyleneandrosta-1,4-diene-3,17-dione), designed as an irreversible, mechanism-based aromatase inhibitor, includes a system of highly electrophilic conjugated Michael acceptor groups. Many agents that induce the cytoprotective phase 2 response of aerobic cells via the Keap1/Nrf2/ARE mechanism also comprise highly electrophilic Michael acceptor groups. This suggested to the present inventors that exemestane might react efficiently with the thiol groups of the reactive cysteine residues of Keap1 involved in the regulation of Nrf2-dependent cytoprotective systems. To the inventors' knowledge, the potential broader pharmacological significance of this aspect of the exemestane structure has not been previously studied.

In addition to its potent mechanism-dependent inhibition of estrogen biosynthesis, in accordance with the embodiments of the present invention, it has now been found that exemestane has novel chemoprotective properties which have hitherto not been recognized. This allows the use of exemestane in medical applications not previously associated with exemestane. These applications would include medical conditions requiring the upgrading of phase-2 gene regulation; downregulation of ROS production; down-regulation of iNOS; and down-regulation of the NF-κb signaling pathway or control of cancers other than female mammary cancer, small cell lung cancer; or pancreatic cancer. The present inventors now show that exemestane can be used for methods of chemoprotection against a wide variety of non-mammary tumors that are not estrogen-dependent, but have oxidative stress, inflammation and electrophile-damaging etiologies.

The present invention also shows that for certain uses described below, exemestane shows powerful synergism with compounds representative of a wide variety of classes of phytochemicals which are Nrf2-activators and phase 2 enzyme gene activators, including, for example sulforaphane (an isothiocyanate), shikonin (a naphthoquinone), zerumbone (a cyclic sesquiterpene) and resveratrol (a stilbene derivative), which increases the attractiveness of exemestane's novel uses.

As will be detailed below, the present inventors now show that the aromatase inhibitor exemestane exhibits a wide range of cytoprotective effects—that appear to be unrelated to aromatase inhibition—and that it potently activates the Keap1-Nrf2-ARE pathway, thereby upregulating expression of genes that regulate an extensive network of inducible cytoprotective phase 2 proteins that protect cells against reactive oxygen species, inflammation, and DNA-damaging electrophiles. In this respect exemestane therefore resembles sulforaphane, the potent chemoprotective isothiocyanate isolated from broccoli and other cruciferous plants that activates the aforementioned Nrf2-dependent phase 2 response.

In accordance with some embodiments, the present invention provides a composition comprising an effective amount of exemestane and/or a derivative or analogue thereof and an effective amount of at least one phase 2 gene activator. It will be understood by those of ordinary skill in the art that the term "phase 2 gene activator" is synonymous with the term "phase 2 enzyme inducer."

In accordance with one or more embodiments, the present invention provides a composition comprising an effective amount of exemestane and/or a derivative or analogue thereof. In accordance with other embodiments, the compositions comprise an effective amount of exemestane and/or a derivative or analogue thereof and at least one phase 2 gene inducer and/or an analogue or derivative thereof.

In accordance with one or more embodiments, the present invention provides a composition comprising an effective amount of exemestane and/or a derivative or analogue thereof and at least one phase 2 gene inducer and/or an analogue or derivative thereof.

In some embodiments, the phase 2 gene inducer and/or an analogue or derivative thereof are selected from the group consisting of isothiocyanates, naphthoquinones, sesquiterpenes and stilbene derivatives.

In further embodiments, the present invention provides a composition comprising an effective amount of exemestane and/or a derivative or analogue thereof and at least one phytochemical derived phase 2 gene inducer and/or an analogue or derivative thereof selected from the group consisting of sulforaphane, shikonin, zerumbone, and resveratrol.

In accordance with another embodiment, the present invention provides a method for the inhibition of inducible nitric oxide synthase (iNOS) in a mammalian subject comprising the administration of the compositions described herein.

In accordance with a further embodiment, the present invention provides a method for the inhibition of NF-κB activation in a mammalian subject comprising the administration of the compositions described herein.

In accordance with still another embodiment, the present invention provides a method for the inhibition of inflammatory cytokines in a mammalian subject comprising the administration of the compositions described herein.

In accordance with an embodiment, the present invention provides a method for the induction of phase 2 related genes in a mammalian subject comprising the administration of the compositions described herein.

In accordance with yet another embodiment, the present invention provides a method for inducing nicotinamide nucleotide:quinone oxidoreductase (NQO1) enzyme activity in a mammalian subject comprising administering a composition comprising an effective amount of the compositions described herein.

In accordance with a further embodiment, the present invention provides a method for the induction of phase 2 related genes in a mammalian subject comprising the administration of a composition comprising an effective amount of the compositions described herein. In a preferred embodiment, the composition comprises exemestane. In another preferred embodiment, the composition comprises administrating exemestane and at least one from among sulforaphane, another glucosinolate or isothiocyanates.

In accordance with still another embodiment, the present invention provides a method for the reduction in reactive oxygen species (ROS) in a mammalian subject comprising the administration of a composition comprising an effective amount of the compositions described herein.

In accordance with yet another embodiment, the present invention provides a method for the treatment of age related macular degeneration (AMD) in a subject comprising administering to the subject a composition comprising an effective amount of the compositions described herein.

In accordance with another embodiment, the present invention provides a method for the treatment of hypoxia/reperfusion related tissue injury in a tissue of a subject comprising administering to the subject a composition comprising an effective amount of the compositions described herein. Preferably, the composition is delivered directly to the affected tissue.

In accordance with an embodiment, the present invention provides a method for the prevention and/or treatment of UV related skin disorders in a subject comprising administering to the skin of a subject a composition comprising an effective amount of the compositions described herein. Preferably, the administration of the composition is a topical application. In another preferred embodiment the composition is delivered systemically, orally or by injection.

In accordance with an embodiment, the present invention provides a method for the treatment of a tumor (other than a mammary gland tumor, a lung small cell tumor or a prostate tumor) in a subject, comprising administering to the subject a composition comprising an effective amount of the compositions described herein.

BRIEF DESCRIPTION OF THE DRAWINGS

(FIG. 1A) Hepa1c1c7; (FIG. 1B) ARPE-19 retinal pigment epithelial cells; (FIG. 1C) 308 keratinocyes; and (FIG. 1D) H9c2 cardiomyocytes. Cells were plated in 96-well plates and 24 hours later were exposed to serial dilutions of exemestane for a further 48 hours. NQO1 activity is expressed as mean ratios of treated over control specific activities by using eight replicate wells for each inducer concentration. Standard deviations for all points were less than 10%. (FIG. 1E) Real-time PCR analysis of phase 2-related genes heme oxygenase-1 (HO-1) and (NQO1) expression after 6 hours of treatment with exemestane in H9c2 cells. β-Actin was used as an endogenous control for the target genes, and the values are represented as the ratio of change in the mRNA levels of the exemestane-treated versus vehicle-treated cells. Means±SD are shown.

(FIG. 3A) ROS suppression by exemestane. After 24 hours of incubation with exemestane, the cells were exposed to 20 µM DCFH-DA for 30 minutes and then challenged with 500 µM tert-butyl hydroperoxide for 30 minutes. Fluorescence intensity was measured as an indicator of oxidation. Means±SD are shown. Protection of ARPE-19 cells against toxicity of (FIG. 3B) tert-butyl hydroperoxide (0.2, 0.4, 0.8 mM for 4 hours) and (FIG. 3C) 4-hydroxynonenal (10, 20, 40 µM for 4 hours) as a function of 24 hours prior exposure to 0-20 µM exemestane. The bar graphs show that cell viability is a function of both the concentrations of the oxidants and of exemestane. Front, center, and rear series of bars refer to the highest, middle, and lowest concentrations of the oxidants, respectively.

(FIG. 6A) Induction of NQO1 as a function of concentration by exemestane or sulforaphane in WT and Nrf2$^{-/-}$ MEF cells. Cells plated in 96-well plates were exposed to serial dilutions of exemestane or sulforaphane for 48 hours. NQO1 activity was determined in cell lysates. (FIG. 6B) Exemestane suppresses ROS production in WT MEF, but not in Nrf2$^{-/-}$ MEF cells. After 24 hours of incubation with exemestane, WT and Nrf2$^{-/-}$ MEF cells were exposed to 20 µM DCFH-DA for 30 minutes, then challenged with 500 µM tert-butyl hydroperoxide for 30 minutes, and fluorescence intensity was measured. Means±SD are shown.

DETAILED DESCRIPTION OF THE INVENTION

Figure 1A:
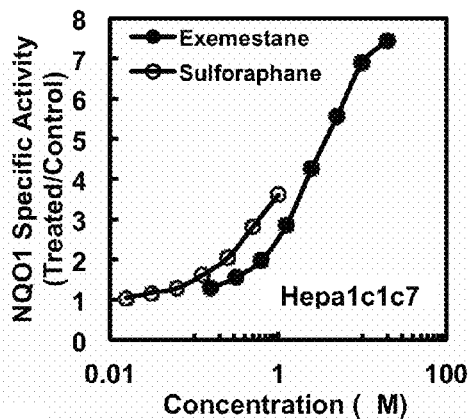
FIGS. 1A-1E illustrate the induction of NAD(P)H: quinone oxidoreductase 1 (NQO1) as a function of concentration by exemestane and sulforaphane in different cell types.
Figure 1B:
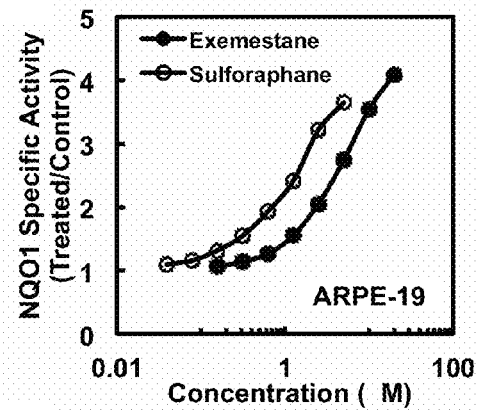
Figure 1C:
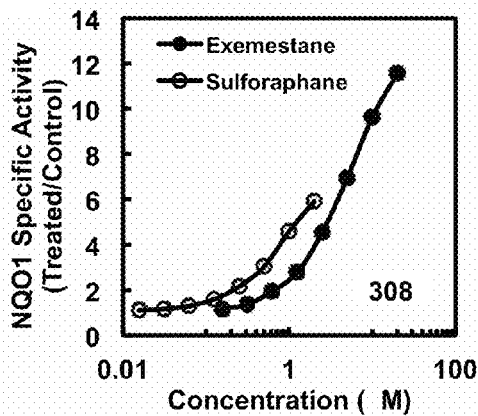
Figure 1D:
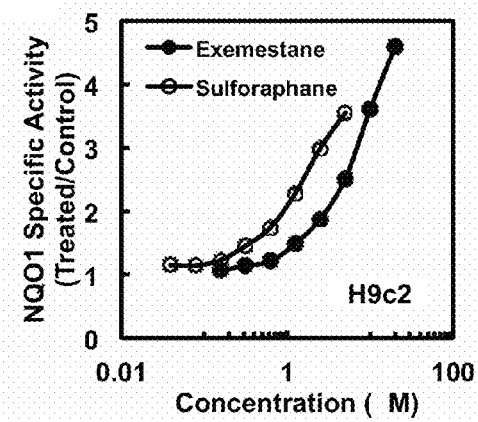

The study, by the present inventors, of the chemical structure of exemestane (6-methyleneandrosta-1,4-diene-3,17-dione) (formula I, below), which was designed as an irreversible, mechanism-based aromatase inhibitor, showed the presence of a system of highly electrophilic conjugated Michael reaction acceptors. This observation suggested to the inventors that exemestane might react efficiently with the thiol groups of the reactive cysteine residues of Keap1 involved in the regulation of Nrf2-dependent cytoprotective genes, or other thiol groups of regulatory molecules. To the inventors' knowledge, the potential broader pharmacological significance and consequences of this aspect of the exemestane structure had not been previously known.

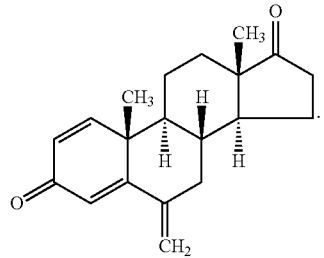
(I)

In accordance with one or more embodiments, the present inventors now show that the aromatase inhibitor exemestane exhibits a wide range of cytoprotective effects that are unrelated to aromatase inhibition, and that exemestane potently activates the Keap1-Nrf2-ARE system, thereby upregulating genes of the cytoprotective phase 2 response. Exemestane therefore protects cells not only against DNA-damaging electrophiles but upregulates major antioxidant and anti-inflammatory mechanisms, and therefore resembles the action of sulforaphane (formula II, below), the potent phase 2 gene activating isothiocyanate isolated from broccoli and other cruciferous plants that activates the Nrf2-dependent phase 2 response.

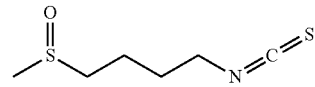
(II)

Exemestane has been administered to women with breast cancer in combination with tamoxifen and suggestions of additive or synergistic effects have been obtained, without enhanced adverse effects. It was understood in the art that these actions involved the blocking of estrogen biosynthesis or estrogen-receptor modulation. This new understanding of other mechanisms of action for exemestane, opens up new clinical applications.

Exemestane shows surprisingly low toxicity in these systems. The present inventors now show that, in addition to its inhibition of estrogen biosynthesis, that exemestane provides much broader cytoprotective activities against oxidative stress and inflammatory processes that contribute also to the etiology of hormonally-independent cancers and many other chronic diseases. Such chronic diseases include: celiac disease, vasculitis, lupus, chronic obstructive pulmonary disease (COPD), irritable bowel disease, atherosclerosis, arthritis, and psoriasis. The present inventors now also show that in some embodiments, exemestane synergizes with phase 2 gene inducers such as sulforaphane in certain protective systems.

As such, in accordance with the embodiments of the present invention, exemestane can therefore be considered for use in chemoprotection against a wide variety of other tumors (and other chronic diseases) that are not estrogen-dependent but have oxidative stress, inflammation and electrophile-damaging etiologies. For example, beyond cancer treatment, exemestane administration can be deployed in situations of chronic or acute inflammations caused by infections or immune hypersensitivity. The additional novel finding that exemestane shows powerful synergism with another Nrf2-activator, sulforaphane, increases the attractiveness of this strategy. These findings were recently published (see, Liu, H. and Talalay, P., Proc. Natl. Acad. Sci. USA, 110:19065-70 (2013).

In accordance with an embodiment, the present invention provides a composition comprising an effective amount of exemestane and/or a derivative thereof and/or an effective amount of exemestane and/or a derivative thereof and a phase 2 gene inducer and/or an analogue or derivative thereof. In some embodiments, there can be more than one phase 2 gene inducer in the compositions of the present invention. In some embodiments, the phase 2 gene inducer can be a phytochemical.

Cells defend themselves against external and internal toxins by increasing the expression of antioxidant/detoxifying genes, the phase 2 enzymes. The phase 2 gene products modify electrophilic intermediates to render them less reactive and harmful as well as increasing the expression of genes that participate in the defensive arsenal. For example, the phase 2 gene product, glutathione (GSH) transferase is a phase 2 enzyme that conjugates hydrophobic electrophiles with GSH, attenuating the electrophile's damaging properties. Another phase 2 enzyme, Quinone Reductase (QR), formally known as NQO1 (NAD(P)H: quinone oxidoreductase 1) promotes the obligatory two-electron reduction of quinones and by this reduction reduces their ability to generate reactive oxygen species and deplete intracellular GSH. Other phase 2 enzymes such as UDP-glucuronosyl-transferases and epoxide hydrolase modify potential reactive species facilitating their excretion. The induction of phase-2 enzymes is also accompanied by the up-regulation of GSH itself.

Phase 2 detoxifying enzymes share a common cis regulatory region, the antioxidant response element (ARE) and its cognate transactivator, NF-E2 related factor 2 (Nrf2). Nrf2 is a cytoplasmic protein but upon induction translocates to the nucleus, binds to other nuclear proteins and participates in phase 2 enzyme gene activation. Edible plants, the cruciferous vegetables such as broccoli, generate high concentrations of potent activators of phase 2 genes, the class of small molecules, the isothiocyanates, sulforaphane [(+1-isothiocyanato-4(R)-(methylsulfinyl)-butane] and its parent compound, the glucosinolates [β-thioglucoside N-hydroximinosulfate, also known as (Z)-(or cis)-N-hydroximinosulfate esters or S-glucopyranosyl thiohydroximates]. A representative listing of glucosinolates and isothiocyanates are found in (Phytochemistry. 2001 January; 56(1):5-51) the contents which are incorporated herein by reference in its entirety.

It is contemplated in one or more embodiments, that the compositions of the present invention can include not only sulforaphane, but other phase 2 gene activators. Representative sulforaphane analogs and derivatives can be found in International Patent Application No. WO2007130353 at Table 2.

There are many other classes of molecules that are phase 2 inducers which can be used in the compositions and methods of the present invention. Many of the useful phase 2 inducing compounds are phytochemicals which are known in the art. For example, shikonin and its derivatives are the main components of red pigment extracts from *Lithospermum erythrorhizon*, which are known in Chinese medicine. Shikonin is a naphthoquinone derivative.

Dozens of naturally occurring shikonin derivatives have been separated and identified hitherto. Most of them are present as ester derivatives linked with the hydroxyl group of the side chain, maintaining the naphthazarin moiety. Since their significant biological activities (especially for anticancer effects) were confirmed, hundreds of shikonin derivatives have already been designed and synthesized. The disclosed patents on shikonin derivatives were mainly divided into two classes: One focused on the modification at 1'-OH, while maintaining its naphthazarin moiety. In fact, part of their structures are same with those naturally occurring ones; Others focused on the double modifications, both at 1'-OH of the side chain and on the naphthazarin moiety.

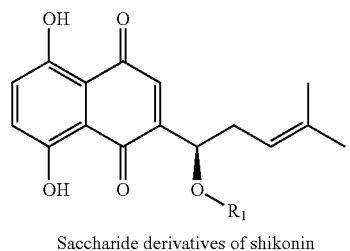

Saccharide derivatives of shikonin

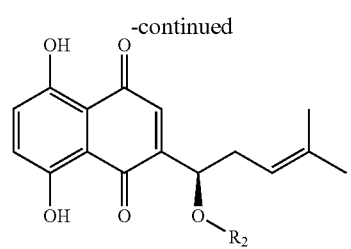

Acetylshikonin derivatives

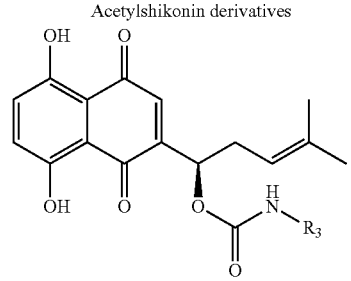

Carbamate derivatives of shikonin

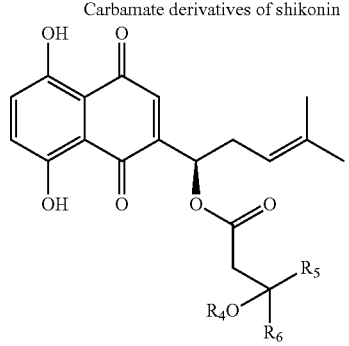

β,β-hydroxyisovalerylshikonin derivatives $R_1$=acetyl-protected five carbon aldose, acetyl-protected six, carbon aldose, acetyl-protected aldehyde disaccharide;

$R_2$=acetyl, β,β-dimethylacryl, isobutyryl, isovaleryl, a-methyl-n-butyryl;

$R_3$=substituted or unsubstituted alkyl and aryl;

$R_4$=H, Me, Et, or acetyl; $R_5$, $R_6$=H, straight alkyl and aryl.

Other shikonin derivatives known include alkannin and their derivatives, which have been investigated as potential anticancer drugs for various aspects of cancer treatment.

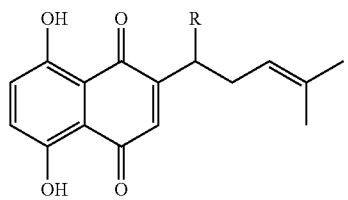

a

| Compound | Abbreviation | R-Group |
|---|---|---|
| Deoxyshikonin | DS | H |
| Shikonin | SK | OH |
| Alkannin | AK | OH |

-continued

| Compound | Abbreviation | R-Group |
|---|---|---|
| Isobutylshikonin | IBS | OCOCH(CH3)2 |
| β,β-dimethylacrylshikonin | DMS | OCOCH=C(CH3)2 |
| Isovalerylshikonin | IVS | OCOCH2CH(CH3)2 |
| α-methyl-n-butylshikonin | MBS | OCOCH(CH3)CH2CH3 |

Alkannin

Shikonin b (a) The chemical structures of shikonin and its analogs. (b) The enantiomeric shikonin and alkannin.

Other phase 2 inducing compounds include members of the class of molecules known as sesquiterpenes. Sesquiterpenes are a class of terpenes that consist of three isoprene units and have the molecular formula $C_{15}H_{24}$. Like monoterpenes, sesquiterpenes may be acyclic or contain rings, including many unique combinations. Sesquiterpenes are found naturally in plants and insects, as semiochemicals, e.g. defensive agents or pheromones. Sesquiterpene lactones (SLs) constitute a large and diverse group of biologically active plant chemicals that have been identified in several plant families such as Acanthaceae, Anacardiaceae, Apiaceae, Euphorbiaceae, Lauraceae, Magnoliaceae, Menispermaceae, Rutaceae, Winteraceae and Hepatideae etc.

There are a wide variety of sesquiterpenes that are known to have biological activity. Without being limited to any particular example, some commonly known sesquiterpenes are shown below.

Geranyl diphosphate    Limonene    Terpinolene

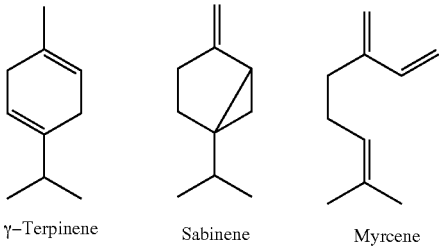

γ-Terpinene    Sabinene    Myrcene

Z-Ocimene    E-Ocimene

The Zingiberaceae family is one of the plant families widely distributed throughout the tropics, particularly in Southeast Asia. In Taiwan, several species of Zingiberaceae plants, such as ginger, *curcuma*, zedoary, and zerunbah, are used as traditional Chinese herbs. Furthermore, many active compounds have been isolated from these plants, such as gingerol, curcumin, yakuchinone A, and zerumbone, all of which exhibit chemopreventive qualities. Zerumbone is a sesquiterpene derived from tropical ginger and contains an electrophilic α,β-unsaturated carbonyl moiety.

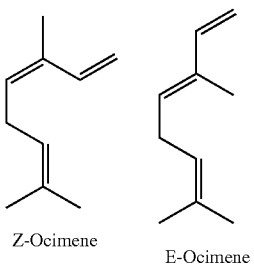

zerumbone

It will be understood by those of ordinary skill in the art, that sesquiterpenes which have phase 2 inducing activity, such as zerumbone, can be used in conjunction with exemestane in the compositions and methods of the present invention.

(E)-Stilbene, is a diarylethene, i.e., a hydrocarbon consisting of a trans ethene double bond substituted with a phenyl group on both carbon atoms of the double bond. Many stilbene derivates (stilbenoids) are present naturally in plants. An example is resveratrol and its cousin, pterostilbene. Resveratrol, a polyphenol found, in particular, in the tannin of wine, is a stilbenic compound (3,5,4'-trihydroxystilbene). Its anti-inflammatory and antioxidant properties have been widely described. Several studies have demonstrated that resveratrol could have beneficial effects on cardiovascular diseases. New stilbene derivatives, such as piceatannol, piceatannol 3'-O—B-d-glucopyranoside (PG), and 3,5,4'-trimethoxystilbene (BTM-0512), have been synthesized.

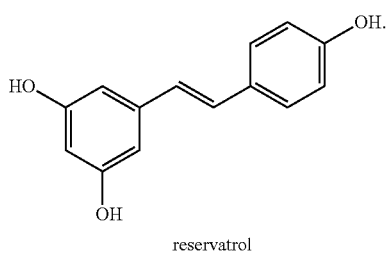 [SMILES: Oc1ccc(/C=C/c2cc(O)cc(O)c2)cc1]

reservatrol

It will be understood by those of ordinary skill in the art, that stillbene derivatives and stilbenoids which have phase 2 inducing activity, such as reservatrol, can be used in conjunction with exemestane in the compositions and methods of the present invention.

In an embodiment, the present invention provides a pharmaceutical composition comprising a compound, salt, solvate, or stereoisomer of exemestane, and a pharmaceutically acceptable carrier. The exemestane composition is used in the treatment or prevention of medical conditions characterized by DNA damaged by electrophiles, oxidation of cellular content, or inflammation.

In an embodiment, the present invention provides a pharmaceutical composition comprising a compound, salt, solvate, or stereoisomer of exemestane, and at least one phase 2 gene inducer, wherein the phase 2 gene inducer is selected from the group consisting of sulforaphane, shikonin, zerumbone, reservatrol, phenethyl isothiocyanate (PEITC), allyl isothiocyanate (AITC), hydroxytyrosol, curcumin, 6-gingerol, capsaicin, genistein, Bis(2-hydroxybenzylidene)acetone (HBB2), Bis(4-hydroxybenzylidene)acetone (HBB4), cyclo-shikonin, deoxyshikonin, plumbagin, and menadione and/or salts, solvates or derivatives thereof.

In another embodiment, the present invention provides pharmaceutical composition comprising a compound, salt, solvate, or stereoisomer of exemestane and at least one additional therapeutic agent, and a pharmaceutically acceptable carrier. Preferably, at least one of the additional therapeutic agents is sulforaphane, another glucosinolate or an isothiocyanate.

Included within the compounds of the present invention are the tautomeric forms of the disclosed compounds, isomeric forms including diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, fumaric acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compositions of the present invention should be pharmaceutically acceptable salts. Other salts may, however, be useful in the preparation of the compounds according to the invention or of their pharmaceutically acceptable salts.

In addition, embodiments of the invention include hydrates of the compositions of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

With respect to the pharmaceutical compositions described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include solid compositions such as solid-state carriers or latex beads.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

The choice of carrier will be determined, in part, by the particular pharmaceutical composition, as well as by the particular method used to administer the composition. Accordingly, there are a variety of suitable formulations of the pharmaceutical composition of the invention.

It will be understood by those of skill in the art that the terms "therapeutic," "preventive," or "protective" agent is any agent capable of affecting the structure or function of the body of a subject or is an agent useful for the treatment or modulation of a disease or condition in a subject suffering therefrom, or at risk thereto. Examples of therapeutic agents can include any drugs known in the art for treatment of disease indications.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se, as well as pharmaceutically acceptable, pharmacologically active salts, esters, amides, prodrugs, metabolites, analogs etc.

The dose of the compositions of the present invention also will be determined by the existence, nature and extent of any adverse side effects that might accompany the administration of a particular composition. Typically, an attending physician will decide the dosage of the pharmaceutical composition with which to treat each individual subject, taking into consideration a variety of factors, such as age, body weight, general health, diet, sex, compound to be administered, route of administration, and the severity of the condition being treated. By way of example, and not intending to limit the invention, the dose of the pharmaceutical compositions of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight.

In another embodiment, the dose of the pharmaceutical compositions of the present invention can be at a concentration from about 100 nM to about 1000 µM, preferably from about 1 µM to about 500 µM, more preferably from about 10 µM to about 50 µM.

The terms "treat," and "prevent" as well as words stemming therefrom, as used herein, do not necessarily imply 100% or complete treatment or prevention of ischemia-reperfusion (IR) injury. Rather, there are varying degrees of treatment or prevention of which one of ordinary skill in the art recognizes as having a potential benefit or therapeutic effect. In this respect, the inventive methods can provide any amount of any level of treatment or prevention of IR injury or cardiac myocyte cell death in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset or slowing the progression of the disease, or a symptom or condition thereof.

The dose of the compositions of the present invention also will be determined by the existence, nature and extent of any adverse side effects that might accompany the administration of a particular composition. Typically, an attending physician will decide the dosage of the pharmaceutical composition with which to treat each individual subject, taking into consideration a variety of factors, such as age, body weight, general health, diet, sex, compound to be administered, route of administration, and the severity of the condition being treated.

As used herein, the terms "effective amount" or "sufficient amount" are equivalent phrases which refer to the amount of a therapy (e.g., a prophylactic or therapeutic agent), which is sufficient to reduce the severity and/or duration of a disease, ameliorate one or more symptoms thereof, prevent the advancement of a disease or cause regression of a disease, or which is sufficient to result in the prevention of the development, recurrence, onset, or progression of a disease or one or more symptoms thereof, or enhance or improve the prophylactic and/or therapeutic effect(s) of another therapy (e.g., another therapeutic agent) useful for treating a disease or condition.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), antioxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-α-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., Pharmaceutics and Pharmacy Practice, J.B. Lippincott Company, Philadelphia, Pa., Banker and Chalmers, eds., pages 238 250 (1982), and ASHP Handbook on Injectable Drugs, Trissel, 15th ed., pages 622 630 (2009)).

Inducible nitric oxide synthase (iNOS) is one of three key enzymes generating nitric oxide (NO) from the amino acid 1-arginine. iNOS-derived NO plays an important role in numerous physiological (e.g. blood pressure regulation, wound repair and host defense mechanisms) and pathophysiological (inflammation, infection, neoplastic diseases, liver cirrhosis, diabetes) conditions. It is contemplated, therefore, that compositions comprising exemestane and/or a derivative thereof, are useful in the treatment of diseases where inflammation is either the origin of the pathology or a subsequent effect.

In accordance with an embodiment, the present invention provides a method for the inhibition of the upregulation of inducible nitric oxide synthase (iNOS) in a cell or population of cells comprising contacting the cell or population of cells with the compositions described herein.

NF-κB is a transcription factor that plays a key role in inflammation. Activation of NF-κB signaling results in expression of pro-inflammatory cytokines as well as iNOS. Therefore, therapeutic agents that can block or inhibit the NF-κB-related signaling pathway and, consequently the production of proinflammatory cytokines may prevent or reduce injury due to inflammation.

In accordance with a further embodiment, the present invention provides a method for the inhibition of NF-κB activation in a cell or population of cells comprising contacting the cell or population of cells with the compositions described herein.

For purposes herein, the compositions of the present invention, which comprise exemestane and a phase-2 inducing enzyme, e.g. sulforaphane, can be used to treat cancer. The cancer can be any cancer. As used herein, the term "cancer" is meant any malignant growth or tumor caused by abnormal and uncontrolled cell division that may spread to other parts of the body through the lymphatic system or the blood stream. The cancer can be any cancer, including any of acute lymphocytic cancer, acute myeloid leukemia, alveolar rhabdomyosarcoma, adenocarcinoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor. Hodgkin lymphoma, hypopharynx cancer, hepatocellular cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

The cancer can be an epithelial cancer. As used herein the term "epithelial cancer" refers to an invasive malignant tumor derived from epithelial tissue that can metastasize to other areas of the body, e.g., a carcinoma. Alternatively, the cancer can be a non-epithelial cancer, e.g., a sarcoma, leukemia, myeloma, lymphoma, neuroblastoma, glioma, or a cancer of muscle tissue or of the central nervous system (CNS).

The cancer can be a non-epithelial cancer. As used herein, the term "non-epithelial cancer" refers to an invasive malignant tumor derived from non-epithelial tissue that can metastasize to other areas of the body.

The cancer can be a metastatic cancer or a non-metastatic (e.g., localized) cancer. As used herein, the term "metastatic cancer" refers to a cancer in which cells of the cancer have metastasized, e.g., the cancer is characterized by metastasis of a cancer cells. The metastasis can be regional metastasis or distant metastasis, as described herein. Preferably, the cancer is a metastatic cancer.

The term "biologically active agent" includes chemotherapeutic agents as well as words stemming therefrom, as used herein, generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle).

Without being limited to any particular example, examples of chemotherapeutic agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids. Further examples include alkylating antineoplastic agents, such as carboplatin and cisplatin; nitrosourea alkylating antineoplastic agents, such as carmustine (BCNU); antimetabolite antineoplastic agents, such as methotrexate; pyrimidine analog antineoplastic agents, such as fluorouracil (5-FU) and gemcitabine; hormonal antineoplastics, such as goserelin, leuprolide, and tamoxifen; natural antineoplastics, such as aldesleukin, interleukin-2, docetaxel, etoposide, interferon; paclitaxel, other taxane derivatives, and tretinoin (ATRA); antibiotic natural antineoplastics, such as bleomycin, dactinomycin, daunorubicin, doxorubicin, and mitomycin; *vinca* alkaloid natural antineoplastics, such as vinblastine and vincristine.

The term "modulate," as used herein means that the expression of the target gene, or level of RNA molecule or equivalent RNA molecules encoding one or more target proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

In accordance with an embodiment, the present invention provides a method for the inhibition of inflammatory cytokines in a cell or population of cells comprising contacting the cell or population of cells with the compositions described herein.

Inflammatory cytokines are often the cause or a symptom of many autoimmune diseases. As such, the autoimmune diseases which can be treated by the methods of the present invention include acute disseminated encephalomyelitis, Addison's disease, Allergies, Alopecia areata, Ankylosing Spondylitis, Antiphospholipid syndrome, Asthma, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune urticaria, Autoimmune uveitis, Cancer, Celiac disease, Chagas disease, Chronic inflammatory demyelinating polyneuropathy, Chronic recurrent multifocal osteomyelitis, Chronic obstructive pulmonary disease, Cold agglutinin disease, Crohn's disease (one of two types of idiopathic inflammatory bowel disease "IBD"), Dermatitis herpetiformis, Dermatomyositis, Diabetes mellitus type 1, Diffuse cutaneous systemic sclerosis, Drug-induced lupus, Discoid lupus erythematosus, Eczema, Endometriosis, Enthesitis-related arthritis, Eosinophilic fasciitis, Gastrointestinal pemphigoid, Glomerulonephritis, Goodpasture's syndrome, Graves' disease, Guillain-Barrésyndrome (GBS), Hashimoto's encephalopathy, Hashimoto's thyroiditis, Idiopathic thrombocytopenic purpura (See Autoimmune thrombocytopenic purpura), Interstitial cystitis Juvenile idiopathic arthritis aka Juvenile rheumatoid arthritis, Kawasaki's disease, Lupus erythematosus, Miller-Fisher syndrome, Mixed connective tissue disease, Morphea, Mucha-Habermann disease aka Pityriasis_lichenoides_et_varioliformis_acuta, Multiple sclerosis, Myasthenia gravis, Myositis, Narcolepsy, Neuromyelitis optica (also Devic's disease), Neuromyotonia, Occular cicatricial pemphigoid, Opsoclonus myoclonus syndrome, PANDAS (pediatric autoimmune neuropsychiatric disorders associated with streptococcus), Paraneoplastic cerebellar degeneration, Paroxysmal nocturnal hemoglobinuria (PNH), *Pemphigus vulgaris*, Pernicious anaemia, Perivenous encephalomyelitis, Polymyositis, Primary biliary cirrhosis, Primary sclerosing cholangitis, Progressive inflammatory neuropathy, Psoriasis, Psoriatic arthritis, Raynaud phenomenon, Relapsing polychondritis, Reiter's syndrome, Restless leg syndrome, Retroperitoneal fibrosis, Rheumatoid arthritis, Rheumatic fever, Sarcoidosis, *Scleroderma*, Serum Sickness, Sjögren's syndrome, Spondyloarthropathy, Still's disease, Stiff person syndrome, Transverse myelitis, Ulcerative colitis (one of two types of idiopathic inflammatory bowel disease "IBD"), Undifferentiated connective tissue disease, Urticarial vasculitis, Vasculitis, Vitiligo, and Wegener's granulomatosis In certain embodiments, the autoimmune disease is selected from a group consisting of inflammatory bowel disease (e.g., ulcerative colitis or Crohn's disease), rheumatoid arthritis, diabetes mellitus, celiac disease, autoimmune thyroid disease, autoimmune liver disease, Addison's Disease, Sjögren's Syndrome, transplant rejection, graft vs. host disease and host vs. graft disease. In certain embodiments, the autoimmune disease is a neurological autoimmune disease, such as multiple sclerosis.

In a further embodiment, the compositions and methods of the present invention can be used in combination with one or more additional therapeutically active agents which are known to be capable of treating conditions or diseases discussed above. For example, the compositions of the present invention could be used in combination with one or more known therapeutically active agents, to treat an autoimmune disease. Non-limiting examples of other therapeutically active agents that can be readily combined in a pharmaceutical composition with the compositions and methods of the present invention are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

An UV protecting agent is a pharmacological or cosmetical agent which protects against the harmful aging effects on skin of UV radiation upon topical application, particularly against actinic keratosis, actinic dermatitis, sunburn, photodermatitis, erythema, UV-induced immunosuppression and their harmful effects related with exposure to light, especially UV light, and photoaging is to be understood herein as including photocarcinogenesis. The UV protecting agent is e.g. a topically applied UV-protecting agent, also commonly designated a sunscreen, or an anti-oxidant or anti-oxidant precursor, or topically applied DNA repair enzymes.

UV-protecting agents (sunscreens) can be e.g. UVA and UVB absorbers, preferably compounds absorbing both UVA (315-400 nm) and UVB (280-315 nm), e.g.: UVB: cinnamates; p-aminobenzoic acid; salicylates; camphor derivatives, such as benzylidene camphor derivatives; benzimidazoles; triazones; etocrylene; octocrylene; and urocanic acid; UVA: benzophenones; camphor derivatives, such as benzylidene camphor derivatives; dibenzoylmethane derivatives; anthralinates; and bisimidazylate; UVA and UVB: anisotriazone, drometrizole trisiloxane, methylene bisbenzotriazolyl tetramethylbutylphenol; and inorganic sunscreens such as titanium dioxide and zinc oxide; e.g. as known under the trademarks Uvinul N-539R (octrylene); Eusolex 232R (phenylbenzimidazole sulfonic acid); Parsol 1789R (avobenzone); Mexoryl SXR (drometizole trisulfonate); Mexoryl XLR (pterethalydene dicamphor sulfonic acid); TinasorbR, e.g. Tinasorb MR (methylene bisbenzotriazol tetramethylbutylphenol), and Tinasorb SR (anizotriazine); combinations of sunscreens with broad spectrum protection and a sun protection factor (SPF) of 15 or higher.

Suitable anti-oxidants or anti-oxidant precursors are e.g.: polyphenols, e.g. tea polyphenols, e.g. green tea or white tea polyphenol extracts; isoflavones, such as genistein; glutathione or a precursor thereof, such as N-acetylcysteine; and tocopherol and tocopherol derivatives.

Further anti-oxidants or anti-oxidant precursors are e.g.: ascorbic acid (vitamin C) and its salts, ascorbyl esters of fatty acids, ascorbic acid derivatives such as magnesium ascorbyl phosphate, sodium ascorbyl phosphate and ascorbyl sorbate; butylated hydroxy benzoic acids and their salts; 6-hydroxy-2,5,7,8-tetramethylchroman-2-carboxylic acid; gallic acid and its alkyl esters, especially propyl gallate; uric acid and its salts and alkyl esters; sorbic acid and its salts; lipoic acid; amines such as N,N-diethylhydroxylamine and aminoguanidine; sulfhydryl compounds such as glutathione; dihydroxyfumaric acid and its salts; lycine pidolate; arginine pilolate; nordihydroguaiaretic acid; biflavonoids; curcumin; lysine; methionine; proline; superoxide dismutase; silymarin; tea extracts; grape skin/seed extracts; melanin; and rosemary extracts.

In some embodiments, the anti-oxidants are tocopherol and tocopherol derivatives, e.g. tocopherol sorbate, especially tocopherol acetate (vitamin E).

While anti-oxidants are exerting their biological function, they may also accessorily confer improved physicochemical stability to the compositions of the invention, e.g. improved stability to oxidation and handling and storage.

In accordance with an embodiment, the compositions of the present invention can be formulated for use as an anti-oxidant type UV protecting agent. In alternative embodiments, the compositions of the present invention can be combined with one or more additional UV protecting agents, including, for example, additional anti-oxidant type UV protecting agents.

Age related macular degeneration (AMD) remains the leading cause of irreversible blindness in the United States and the Developed World. It has been calculated that, with the aging of the United States population, the prevalence of the disease will reach epidemic proportions, with an estimated 3 million United States citizens having the advanced form of the disease by 2020.

AMD is a single disorder which is often characterized as one of two types, non-exudative (dry form) or exudative (wet form). Although both types are bilateral and progressive, each type may reflect different pathological processes.

Both exudative (wet form) and non-exudative (dry form) of AMD are typically accompanied by the formation of drusen. Drusen are characterized by irregular, discrete, round yellow-white deposits which accumulate in the retina (back of the eye) between the basement membrane of the retinal pigment epithelium (RPE) and the rest of Bruch's membrane. The presence of drusen most likely reflect abnormalities in retinal pigment epithelial function. Drusen deposits can be further categorized into hard drusen or soft drusen.

Exudative (wet form) AMD is characterized by serous or hemorrhagic separation of the retinal pigment epithelium or neurosensory layer. Patients may develop choroidal neovascularization (CNV), which is manifested as fluid accumulation, hemorrhage, and/or lipid exudation.

The earliest stage of diabetic retinopathy DR is characterized by retinal vascular abnormalities including microaneurysms (saccular out-pouchings from the capillary wall), intraretinal hemorrhages, and cotton-wool spots (nerve fiber layer infarctions). As the disease progresses, the gradual closure of retinal vessels results in retinal ischemia, giving rise to signs including venous abnormalities (beading, loops), intraretinal microvascular abnormalities, and increasing retinal hemorrhage and exudation. Non-proliferative diabetic retinopathy is graded as mild, moderate, severe, and very severe according to the presence and extent of the above lesions.

The more advanced stage of DR involves the formation of new blood vessels, induced by the retinal ischemia, which spreads out either from the disc (neovascularization of the disc, NVD) or from elsewhere in the retina (neovascularization elsewhere, NVE). New vessels extending into the vitreous can cause vitreous hemorrhage, and tractional retinal detachments associated with accompanying contractile fibrous tissue.

To date, the only treatment conclusively demonstrated to be of long term benefit for DR is focal laser photocoagulation.

The standard treatment for patients with AMD is injections of anti-VEGF into the eye, and there have been studies that have shown that anti-VEGF therapy may be useful in DR.

It is contemplated that the patients to be treated using the methods of the present invention are suffering from AMD or DR. In accordance with an embodiment, the present invention provides a method for the treatment of age related macular degeneration (AMD) in a subject comprising administering to the subject the compositions described herein.

As used herein, the term "IR injury" means microvascular dysfunction that is manifested as impaired endothelium-dependent dilation in arterioles, enhanced fluid filtration and leukocyte plugging in capillaries, and the trafficking of leukocytes and plasma protein extravasation in postcapillary venules. Activated endothelial cells in all segments of the microcirculation produce more oxygen radicals, but less nitric oxide, in the initial period following reperfusion. The resulting imbalance between superoxide and nitric oxide in endothelial cells leads to the production and release of inflammatory mediators (e.g. platelet-activating factor, tumor necrosis factor) and enhances the biosynthesis of adhesion molecules that mediate leukocyte-endothelial cell adhesion. Some of the known risk factors for cardiovascular disease (hypercholesterolemia, hypertension, and diabetes) appear to exaggerate many of the microvascular alterations elicited by ischemia and reperfusion. The inflammatory mediators released as a consequence of reperfusion also appear to activate endothelial cells in remote organs that are not exposed to the initial ischemic insult. This distant response to IR injury can result in leukocyte-dependent microvascular injury that is characteristic of the multiple organ dysfunction syndrome. Often in cardiac tissue, the resulting IR injury is the cause of subsequent heart failure. Reperfusion injury may be responsible for up to 50% or more of the ultimate infarct size and is an important contributor to post-surgical mortality and morbidity as well. Clinically, the extent of myocardial salvage by early reperfusion may not be realized because of cell injury and death initiated by reperfusion itself. The term "IR injury" can also mean damage caused during organ transplantation, such as cardiac, renal, lung, and hepatic transplantation.

In accordance with an embodiment, the present invention provides a method for the treatment of hypoxia/reperfusion related tissue injury in a tissue of a subject comprising administering to the subject the compositions described herein.

In accordance with an embodiment, the additional therapeutic agent can be an agent that can mitigate or prevent IR injury, or another cardiac therapeutic agent. Examples of agents which mitigate or prevent IR injury include, for example, allopurinol, adenosine, oxygen free radical scavengers, antioxidants, inhibitors of neutrophils, nitric oxide, adenosine-related agents, inhibitors of the renin-angiotensin system, endothelin receptor antagonists, $Na^+/H^+$ exchange inhibitors, and anti-apoptotic agents, such as IL-10.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

As used herein, the term "cell or population of cells can mean cells from a subject which are treated with the compositions described herein either in vivo or in vitro.

EXAMPLES

Materials and Methods

Chemicals. Exemestane and letrozole were purchased from LKT Laboratories (St. Paul, Minn.). R,S-sulforaphane was from Santa Cruz Biotechnology (Santa Cruz, Calif.). Tamoxifen was obtained from Cayman Chemical (Ann Arbor, Mich.). MTT, tert-butyl hydroperoxide, sodium hydrosulfite ($Na_2S_2O_4$), 2',7'-dichlorodihydrofluorescein diacetate ($H_2DCFDA$) and other chemicals were from Sigma-Aldrich (St. Louis, Mo.). All cell culture media and fetal bovine serum (FBS) were obtained from Invitrogen (Life Technologies, Carlsbad, Calif.).

Cell Cultures. All cell lines were maintained in 5% $CO_2$ at 37° C. in the following media: α-MEM supplemented with 10% heat- and charcoal-treated FBS (murine hepatoma Hepa1c1c7 cells), DMED (high glucose) supplemented with 10% heat-inactivated FBS (murine macrophage-like RAW264.7 cells and rat H9c2 myocardiocytes), a mixture of equal volumes of DMEM and Hanks' F-12 medium supplemented with 10% heat- and charcoal-treated FBS (human adult retinal pigment epithelial ARPE-19 cells), or MEM (2 mM L-glutamine) supplemented with 10% heat-treated FBS and 1% non-essential amino acids (murine 308 keratinocytes). Mouse embryonic fibroblasts (MEF) derived from day 13.5 embryos of wild type or Nrf2-knockout (Nrf−/−) C57BL/6 mice (Proc Natl Acad Sci USA 101: 2040-2045 (2004)) were grown in Iscove's modified Dulbecco's medium plus 10% heat-inactivated FBS. The stably transfected human monocytic U937 cells with an NF-κB reporter construct, which contains the luciferase reporter gene regulated by a promoter containing three NF-κB sites (U937-3× κB-LUC cells) (J Immunol 168: 1441-1446 (2002)), were maintained in RPMI 1640 (2 mM L-glutamine) supplemented with 10% heat-inactivated FBS, 50 Um' penicillin, 50 ng/ml streptomycin and 75 ng/ml hygromycin B to ensure selection of cells that retained the construct.

NQO1 Assay. Cells (10,000 per well) were grown in 96-well plates for 24 hours, then exposed to serial dilutions of inducers for 48 hours, and lysed in 0.08% digitonin. Enzymatic activity of NQO1 in cell lysates was determined with menadione as a substrate (Anal Biochem 169: 328-336 (1988), Methods Enzymol 382(B): 243-258 (2004)). The concentrations required to double the specific activity of NQO1 (CD values) were used to quantify inducer potency.

mRNA isolation and real-time PCR analysis. H9c2 cells (100,000 per well) were grown in 6-well plates for 24 hours, then exposed to vehicle or 10 mM exemestane for 6 hours. Total mRNA from cells was extracted with TRIzol reagent (Invitrogen, Carlsbad, Calif.). DENA was synthesized by the iScript cDNA Synthesis Kit (Bio-Rad Laboratories, Inc., Hercules, Calif.). Quantitative real-time PCR analysis was performed using the 7000 Sequence Detection System (Applied Biosystems, Foster City, Calif.). All primers were optimized and a final primer concentration of 300 nM was used for all reactions. Primer sequences for gene amplification were as follows: NAD(P)H: quinone oxidoreductase 1 (NQO1): fwd 5'-tccagaaacgacatcacagg-3' (SEQ ID NO: 1), rev 5'-ttcagctacaatatccgggc-3' (SEQ ID NO: 2); heme oxygenase-1 (HO-1): fwd 5'-cagggtgacagaagaggctaagac-3' (SEQ ID NO: 3), rev 5'-tgaggacccatcgcaggag-3' (SEQ ID NO: 4). β-actin (endogenous control): fwd 5'-ccccatt-gaacacggcatt-3' (SEQ ID NO: 5), rev 5'-catcttttcacggttggc-ctta-3' (SEQ ID NO: 6). The reactions were assembled using 5 ng of cDNA, 1×Power SYBR Green PCR Master Mix (Life Technologies), forward and reverse primers, and nuclease-free water. Relative mRNA expression was normalized to β-actin. Gene expression was calculated using the comparative $2^{-\Delta\Delta C_T}$ method.

NQO1 Induction in Mouse Skin. Eleven-month-old female SKH-1 hairless mice (n=5) purchased from Charles River Laboratories were treated three times at 24-hour intervals on the backs with 0, 1 and 2 μmol of exemestane dissolved in 80% aqueous acetone (40 μL) over about a 2.0 $cm^2$ area. Mice were euthanized 24 hours after the final dose. Each treated segment of the dorsal skin was harvested, pulverized in liquid $N_2$, and homogenized in 10 volumes of 0.25 M sucrose in 10 mM Tris buffer (pH 7.4). After three freeze-thaw cycles, the homogenates were centrifuged at 14,000 rpm and 4° C. for 30 minutes, and the supernatant fractions were analyzed for protein concentration and NQO1 activity. All animal experiments were in compliance with National Institutes of Health Guidelines and were approved by The Johns Hopkins University Animal Care and Use Committee.

Detection of Intracellular Reactive Oxygen Species (ROS). ARPE-19 or MEF cells (10,000 per well) in 96-well plates (black-walled wells with clear bottom) were treated with serial dilutions of exemestane for 24 hours, and then incubated with 20 μM $H_2DCFDA$ for 30 minutes (Chem Res Toxicol 5: 227-231(1992)). After washing with Dulbecco's phosphate-buffered saline (DPBS) twice, the cells were challenged with 500 μM tert-butyl hydroperoxide for 30 minutes, and fluorescence intensity was measured in SpectraMax GeminiEM plate reader (Molecular Devices) with excitation at 485 nm and emission at 530 nm. Murine 308 keratinocytes (40,000 per well) were plated in 24-well plates and grown for 24 hours. Medium was then replaced with medium containing different concentrations of exemestane (0, 2, 4, 8 μM). After further incubation for 24 hours, cells were incubated with 20 μM $H_2DCFDA$ for 30 minutes, washed twice with DPBS twice and exposed to 5 or 10 $J/cm^2$ UVA (340-400 nm). Immediately after UVA irradiation, fluorescence intensity was measured by a microplate reader.

Measurement of Cytotoxicity of Oxidative Stresses. ARPE-19 cells (10,000 cells/well) in 96-well plates were treated with serial dilutions of exemestane for 24 hours, and exposed to tert-butyl hydroperoxide or 4-hydroxynonenal in serum-free medium for 4 hours. The cells were then incubated in serum-free medium for additional 20 hours, washed with DPBS, and cell viability was determined using the colorimetric procedure based on the reduction of a water-soluble tetrazolium salt, 3-(4,5-dimethylthiazo-2-yl)-2,5-diphenyltetrazolium bromide (MTT). H9c2 cells (10,000 cells/well) in 96-well plates were treated with a range of concentrations of exemestane. After 24 hours, the cells were washed with DPBS, and exposed to 2 mM $Na_2S_2O_4$ in serum-free medium for 1 hour. The cells were then washed with DPBS and incubated in complete medium containing 10% FBS for 24 hours, and then cell viability was measured by the MTT assay.

Preparation of Peritoneal Macrophages from Nrf2−/− Mice. Nrf2−/− mice on C57BL/6 background were initially established by Itoh et al. WT C57BL/6 mice were purchased from The Jackson Laboratory. Macrophages were harvested by lavage from the peritoneal cavity with DPBS 4 days after an i.p. injection of thioglycolate broth (Brewer. 4%), Isolated cells were plated into 96-well plates at a density of $10^5$ cells per well in RPMI 1640 medium containing 2 mM Lglutamine, 10% heat-inactivated FBS, 100 U/ml penicillin, and 100 µg/ml streptomycin. After 3 hours of incubation at 37° C. in 5% $CO_2$, nonmacrophage cells were washed away with DPBS. The remaining macrophages were exposed immediately to serial dilutions of exemestane, sulforaphane or a combination of both compounds in the presence of 100 ng/ml LPS, and incubated for 24 hours before measurement of iNOS.

Measurement of iNOS Induction. RAW264.7 cells (20,000 per well) in 96-well plates, were grown for 24 hours, and exposed to serial dilutions of exemestane in the presence of 10 ng/ml LPS. After 48-hour incubation, nitrite concentration in culture supernatant fractions of RAW264.7 cells or mouse peritoneal macrophages, measured as an indicator of iNOS induction, was determined by the Griess reaction (Cancer Res 58: 717-723 (1998), Proc Natl Acad Sci USA 105: 15926-15931 (2008)). The nitrite values of cells treated with LPS but without test compounds were used as controls.

Measurement of Luciferase Activity. Human monocytic U937-3×κB-LUC cells were transferred to medium with 2% heat-inactivated FBS in 24-well plates ($1 \times 10^6$ cells/well) and incubated overnight. Then cells were incubated with exemestane, sulforaphane, combination of both compounds, or vehicle control for 30 minutes, and exposed to LPS (10 ng/ml). After an additional 6-hour incubation, cells were harvested and NF-kB-driven luciferase activity was assayed according to the manufacturer's instructions (Promega, Madison, Wis.). Luciferase activity was normalized to total protein concentration to compensate for possible cell toxicity of the compounds.

Example 1

Exemestane Induces NQO1 Transcription and Activities in Cultured Cells

The Activity is not Dependent on Aromatase Inhibition.
The inventors first confirmed that exemestane induces the activity of NQO1, a prototypic phase 2 enzyme. In murine hepatoma Hepa1c1c7 cells, human retinal pigment epithelial ARPE-19 cells, murine keratinocyte 308 cells, and rat H9c2 myocardiocytes, inducer potencies of exemestane were comparable with, although modestly lower than, those of sulforaphane. The CD values for exemestane were 0.65 µM in Hepa1c1c7 and 308 cells, 2.2 µM in ARPE-19 and 2.9 µM in H9c2 cells, whereas the corresponding CD values for sulforaphane were 0.2 µM in Hepa1c1c7 and 308, 0.7 µM in ARPE-19, and 0.9 µM in H9c2, respectively. An impressive property of exemestane was its low toxicity. In all cell lines, exemestane showed no cytotoxicity up to 20 µM, the highest concentration tested, and increases in specific activities of NQO1 up to 4- to 12-fold were observed (FIG. 1A, B, C, D). Exemestane therefore shows a very high Chemoprotective Index as defined by Pezzuto and colleagues (Characterization of natural product chemopreventive agents. In: Cancer Chemoprevention 2 (pp. 3-37). Strategies for Cancer Chemoprevention. G J Kelloff, E T Hawk, C C Sigman (eds.), Humana Press, Totowa, N.J. (2005)).

To evaluate the effect of the combination of exemestane and sulforaphane on induction of NQO1, Hapa1c1c7 cells were treated with mixtures of the two agents at constant ratios. Exemestane and sulforaphane showed no clear synergism on NQO1 induction at both 2:1 and 5:1 molar ratios. The mode of interaction is mostly additive (data not shown), which suggests strongly that exemestane induces NQO1 activity through the same Keap1/Nrf2/ARE mechanism as sulforaphane.

To evaluate whether the phase 2 enzyme inducer activity of exemestane depends on aromatase inhibition, letrozole, a nonsteroidal aromatase inhibitor with totally different chemical structure from exemestane was selected. In Hepa1c1c7 cells and at concentrations up to 20 µM, letrozole showed no inducer activity for NQO1. In the same system, tamoxifen did not induce NQO1 activity but showed about 90% cytotoxicity at 20 µM.

Figure 1E:
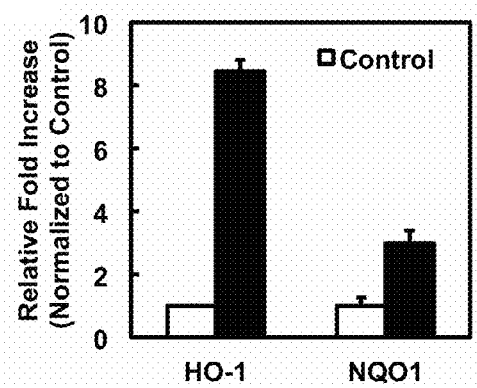

Next, the inventors determined whether treatment with exemestane changed expression of cytoprotective phase 2-related mRNA levels of heme oxygenase 1 (HO-1) and NQO1 in H9c2 cardiomyocytes. Real-time PCR analysis of 10 µM exemestane-treated cells showed a significant (greater than 8-fold increase) in the mRNA levels of HO-1, and a 3-fold increase in NQO1 expression over the control cells (FIG. 1E). These results establish that exemestane treatment transcriptionally upregulates the protective phase 2 response that contributes to its antioxidative stress and anti-inflammatory activities.

Example 2

Exemestane Induces NQO1 Activity In Vivo, on Mouse Skin

Figure 2:
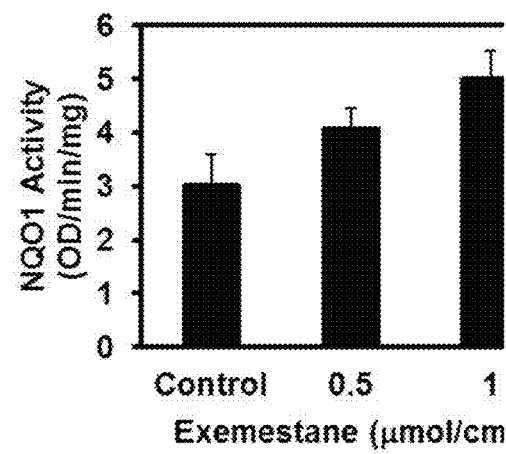
FIG. 2 shows induction of NQO1 in mouse skin by topical application of exemestane. The back of each SKH-1 hairless mouse (n=5) was topically treated with two concentrations of exemestane (in 80% acetone) and solvent only over about a 2.0 $cm^2$ area for three doses at 24-hour intervals. Mice were euthanized 24 hours after the last dose, and dorsal skin was harvested. NQO1 specific activity was measured in supernatant fractions of homogenates of skin sections treated with exemestane or solvent (control). Means±SD are shown.

The ability of exemestane to induce the cytoprotective enzyme NQO1 in the skin of female SKH-1 hairless mice was evaluated next. These mice are immunocompetent but hairless because of a defect in the keratin biosynthesis cycle. Three topical applications of exemestane (0.5 or 1.0 µmol/$cm^2$ per application) at 24-hour intervals to the dorsal skin of SKH-1 mice (n=5) substantially elevated NQO1 activity (1.3- and 1.7-fold, respectively) in homogenates of skin (FIG. 2).

Example 3

Exemestane Protects Human Retinal Pigment Epithelial Cells, Mouse Keratinocytes and Rat Myocardiocytes Against Oxidative Damage Age-related macular degeneration (AMD) is the leading cause of blindness among the elderly in developed countries.

Figure 3A:
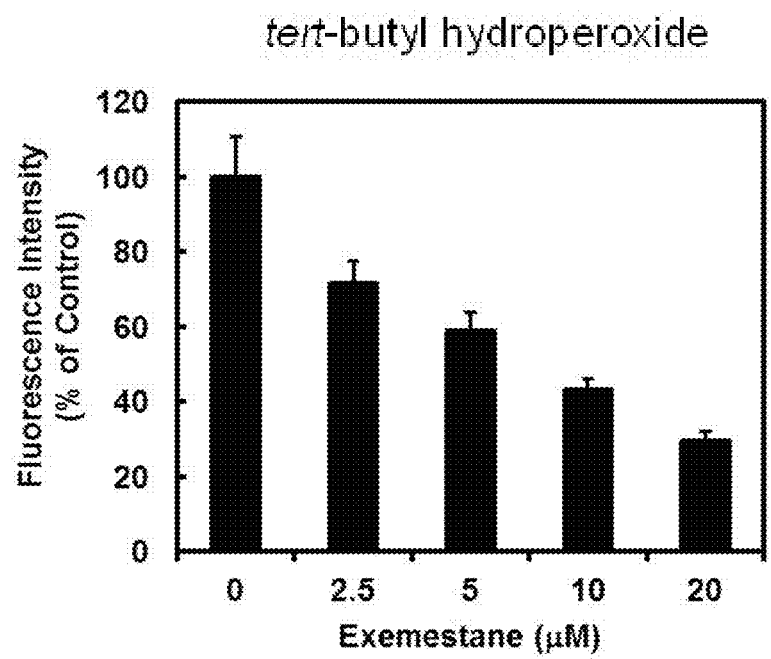
FIGS. 3A-3C illustrate that exemestane protects human retinal pigment epithelial ARPE-19 cells against oxidative stress.
Figure 3B:
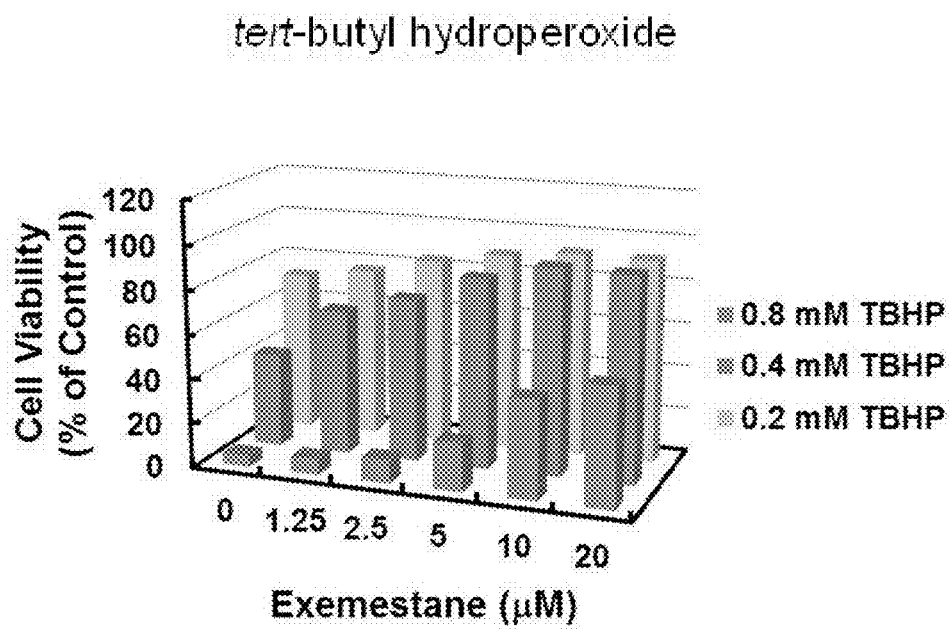
Figure 3C:
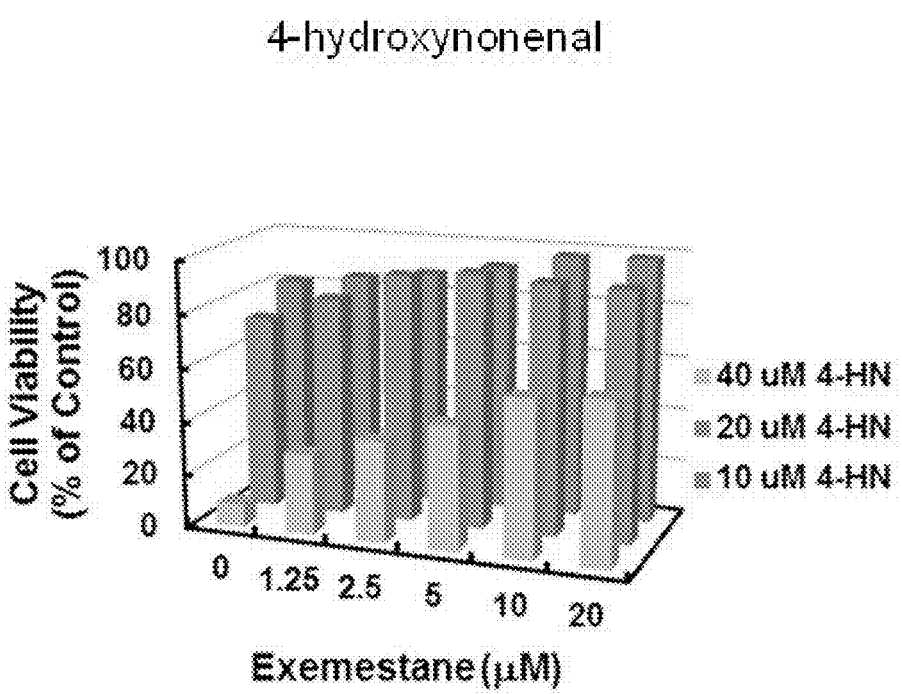

In AMD, pathologic changes in the retinal pigment epithelium (RPE) have been observed early in the disease process, and reactive oxygen species (ROS) may be involved in RPE cell dysfunction and contribute to the development of AMD. The inventors tested whether exemestane could reduce ROS production in ARPE-19 by using the fluorescence-generating probe 2',7'-dichlorodihydro-fluorescein diacetate ($H_2DCFDA$). The results showed that prior treatment with exemestane suppressed ROS production stimulated by tert-butyl hydroperoxide in a dose-dependent manner (FIG. 3A). Treatment of ARPE-19 cells with a range of concentrations of exemestane for 24 hours, also protected against cytotoxicity of oxidants (tert-butyl hydroperoxide and 4-hydroxynonenal, FIGS. 3B and 3C, respectively). These protections depend on concentrations of both the oxidants and exemestane (FIGS. 3B, 3C).

Example 4

Protection Against Ultraviolet Radiation

Figure 4:
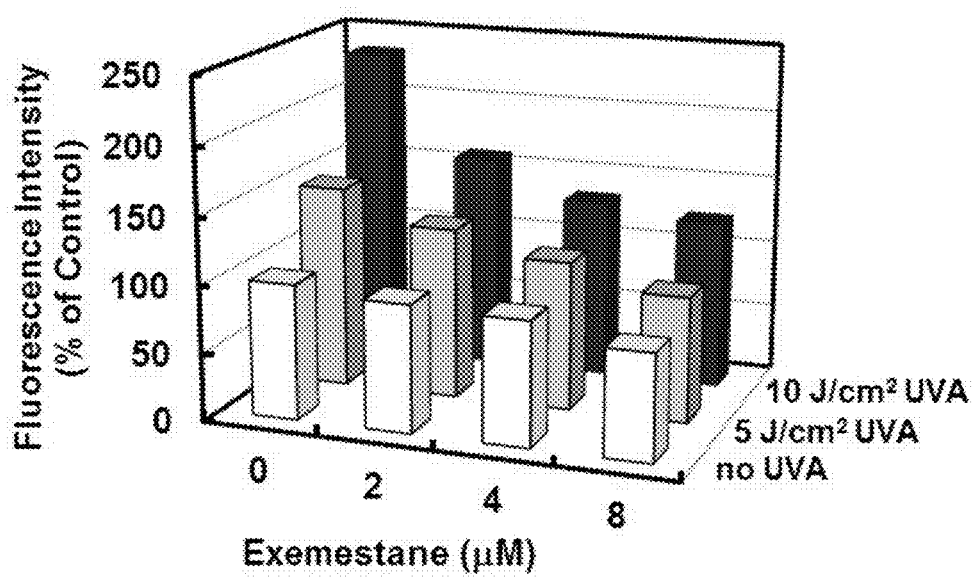
FIG. 4 depicts exemestane inhibiting UVA-stimulated ROS production in murine 308 keratinocytes. Cells plated in 24-well plates were pretreated with exemestane for 24 hours. After incubation with 20 µM DCFH-DA for 30 minutes, cells were exposed to 5 or 10 $J/cm^2$ UVA, and fluorescence intensity was measured as indicator of ROS production in the cells. Cells that received no treatment were set as control. Standard deviations for all points were less than 10%.

UVA radiation (320-400 nm) comprises more than 95% of solar radiation that reaches the surface of the earth, and has deleterious effects on the skin. In response to UVA exposure, ROS are generated, which may directly result in damage to cellular proteins, lipids and saccharides, and may also indirectly cause structural damage of DNA. Consequently the incidence of skin diseases, such as skin aging and skin cancer, has been dramatically increasing, and inhibition of UVA-induced oxidative stress may contribute to the prevention of skin diseases. To evaluate the potential UVA-protective effects of exemestane, mouse 308 keratinocytes were treated with exemestane 24 hours before UVA irradiation, and ROS levels were measured by using $H_2DCFDA$. As shown in FIG. 4, exemestane treatment dose-dependently led to the reduction of ROS in the irradiated 308 cells.

Example 5

Protection Against Hypoxia-Reoxygenation Injury

Figure 5:
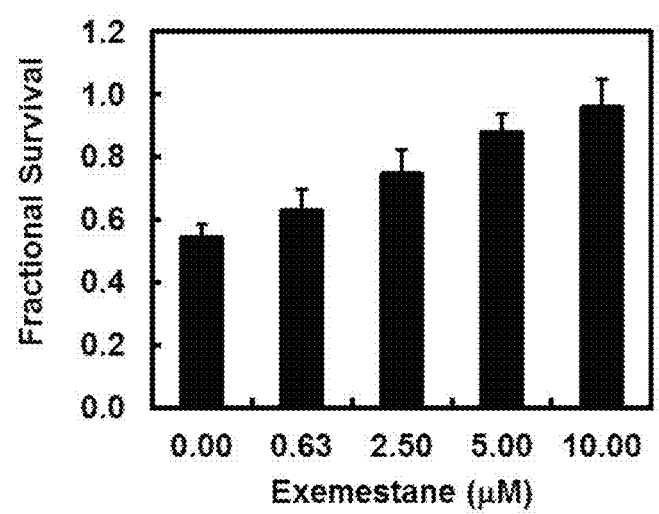
FIG. 5 shows that exemestane protects against hypoxia/reoxygenation-induced cardiomyocyte injury. Rat myocardial H9c2 cells were pretreated with exemestane for 24 hours. Cells were subjected to hypoxia for 1 hour (2 mM $Na_2S_2O_4$) and reoxygenation for 24 hours. Cell viability, assessed by MTT assay, was expressed as fractional survival compared to cells without hypoxia/reoxygenation. Means±SD are shown.

Cellular injury resulting from ischemia and reperfusion (IR) is a major contributor to morbidity and mortality of many diseases including myocardial infarction, ischemic stroke, and circulatory arrest. IR injury is also a major complication of certain therapeutic procedures including organ transplantation and cardiovascular surgery. Damage during reperfusion is believed to arise largely from the generation of ROS, leading to oxidative stress, and inflammation. A hypoxia/reoxygenation model was used to mimic IR injury in H9c2 rat cardiomyocytes and to evaluate the protection by exemestane. Treatment of H9c2 cells with a range of concentrations of exemestane (0, 0.63, 2.5, 5, and 10 µM) for 24 hours, protected against hypoxia/reoxygenation injury in a dose-dependent manner, and almost totally restored cell viability at 10 µM concentration (FIG. 5).

Example 6

Exemestane Activity Depends on the Keap1/Nrf2 Pathway

Figure 6A:
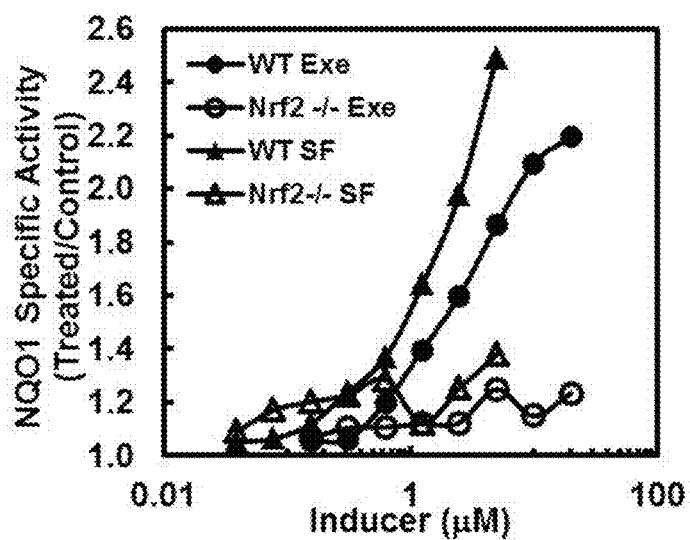
FIGS. 6A-6B depict that Nrf2 is essential for exemestane to induce phase 2 response and suppress ROS production.
Figure 6B:
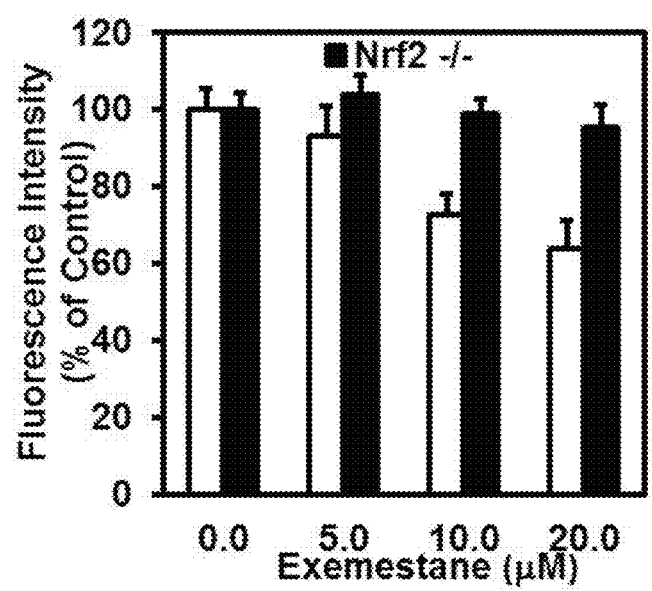

To confirm that exemestane induces NQO1 via the Nrf2 transcription factor, the inventors examined NQO1 induction by bioassay with exemestane in mouse embryonic fibroblasts (MEF) derived from wild-type or Nrf2-knockout mice. Like sulforaphane, exemestane dose-dependently induced NQO1 activity in wild-type MEF. In sharp contrast, in Nrf2-knockout ($Nrf2^{-/-}$) MEF, NQO1 activity was not affected by either sulforaphane or exemestane (FIG. 6A). The inventors also examined the protection by exemestane against oxidative stress and its dependence on Nrf2 gene function by measuring tert-butyl hydroperoxide-stimulated ROS generation in MEF cells. The levels of ROS observed in wild-type MEF were clearly suppressed by exemestane, whereas exemestane showed no protection in $Nrf2^{-/-}$ MEF (FIG. 6B). The results establish that exemestane protects against oxidative stress through the Keap1/Nrf2 pathway.

Example 7

Exemestane Inhibits LPS-Activated iNOS in Macrophages

Figures 7A, 7B:
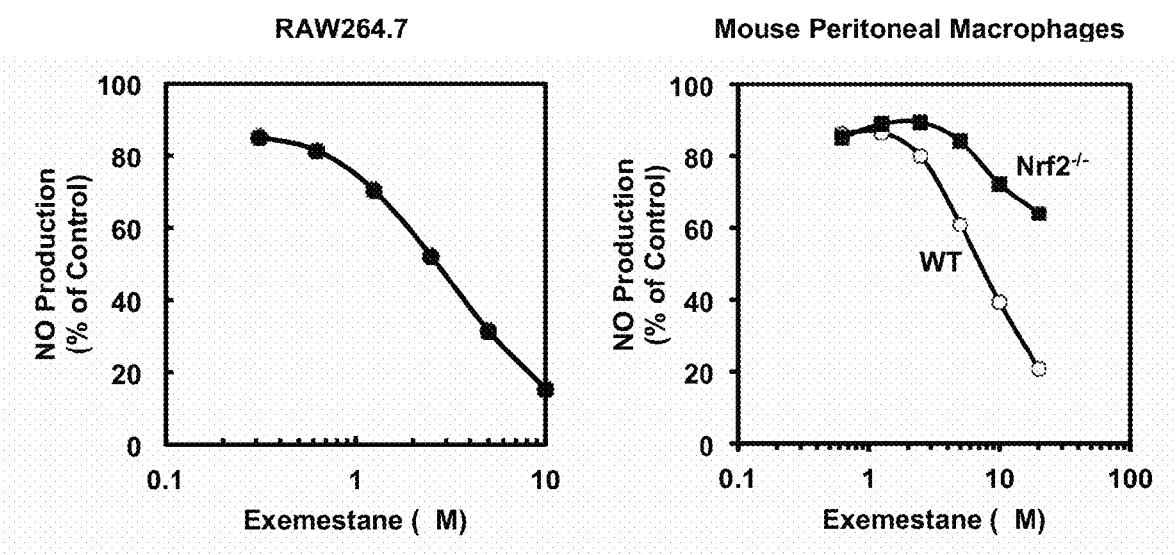
FIGS. 7A-7B show the effects of exemestane on LPS-activated iNOS activity (NO production) in RAW264.7 cells (FIG. 7A), and WT and Nrf2-/- mouse peritoneal macrophages (FIG. 7B). Cells in 96-well plates were exposed to serial dilutions of exemestane in the presence of 10 ng/ml LPS for 48 h (RAW264.7) or 100 ng/ml LPS for 24 hours (peritoneal macrophages). Then NO production was measured as nitrite accumulation in the medium by the Griess reaction. Control cells were treated with LPS only. Standard deviations for all points were less than 10%.

In addition to inducing phase 2 enzymes, a broad range of inducers from different chemical classes have shown anti-inflammatory activities. Inducible nitric oxide synthase (iNOS) has been recognized as an inflammatory biomarker, and induction of iNOS contributes to cell injury in various diseases. Expression of iNOS can be induced by inflammatory mediators such as the bacterial endoxin LPS, through the IKK/NF-κB pathway. To explore the anti-inflammatory potential of exemestane, the inventors quantified the ability of exemestane to suppress the LPS-dependent transcriptional activation of iNOS by measuring the NO produced by iNOS by the Griess reaction in RAW264.7 macrophage-like cells. Exemestane inhibited NO generation dose-dependently with an $IC_{50}$ value of 2.5 µM, modestly less potent than sulforaphane in this assay ($IC_{50}$=0.5 µM) (FIG. 7A). For comparison, both letrozole and tamoxifen (up to 20 µM concentration) did not inhibit LPS-stimulated NO production in RAW264.7 cells. In this system, tamoxifen was 50% cytotoxic at 20 µM whereas exemestane and letrozole showed no toxicity at the same concentration. These results indicate that the anti-inflammatory effect of exemestane does not relate to estrogen function modification.

Since the Keap1/Nrf2/ARE pathway is essential for phase 2 gene inductive and antioxidative activities of exemestane, the inventors further examined whether this pathway is also obligatory for its anti-inflammatory activity. The inventors compared inhibition of LPS-dependent up-regulation of iNOS by exemestane in peritoneal macrophages from wild type and $Nrf2^{-/-}$ mice. Unlike sulforaphane, which inhibited LPS (100 ng/ml)-stimulated NO production with similar potencies in both cell types, exemestane was much less effective inhibitor of NO production in $Nrf2^{-/-}$ macrophages than it was in WT macrophages (FIG. 7B). This finding suggests that the inhibition of the upregulation of iNOS by exemestane is mainly dependent on Nrf2. Accordingly, although both sulforaphane and exemestane have antiinflammatory activities, they exercise their effects via different mechanisms.

Example 8

Figure 8:
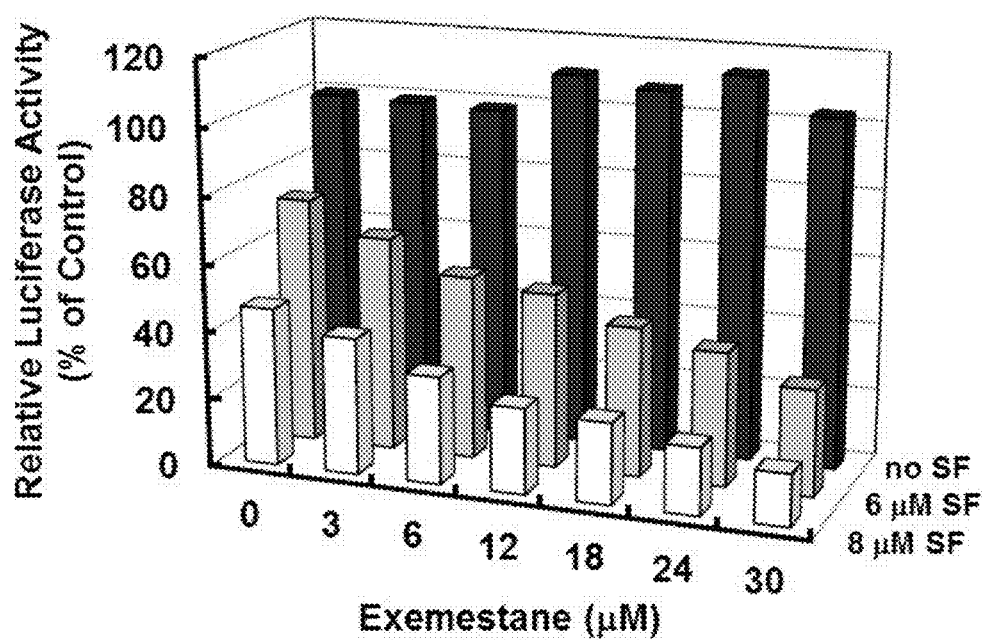
FIG. 8 illustrates the effects of exemestane, sulforaphane and their combination on LPS-induced NF-κB reporter gene activity. U937 3×κB-LUC cells were incubated with exemestane, sulforaphane, or their combination for 30 minutes, LPS (10 ng/ml) was added and the NF-κB-driven luciferase activity was measured after 6 hours of LPS exposure. Luciferase activity was normalized to LPS control (100%). Each bar represents the mean of triplicate experiments. Standard deviations for all points were less than 10%.

Exemestane Enhances the Inhibition of Sulforaphane on NF-κB Activation in U937 Cells NF-κB is a transcription factor that plays a key role in inflammation. Activation of NF-κB signaling results in expression of pro-inflammatory cytokines as well as iNOS. Therefore, therapeutic agents that can block or inhibit the NF-κB-related signaling pathway and, consequently the production of proinflammatory cytokines may prevent or reduce injury due to inflammation. A human monocyte cell line (U937) stably transfected with a luciferase reporter containing three NF-κB binding sites was used to evaluate the ability of exemestane to suppress NF-κB activation by LPS as measured by generation of ROS in these cells. As shown in FIG. 8, exemestane had no effect on LPS-activated NF-κB at up to 30 µM concentration. Nonetheless, it dramatically enhanced the inhibitory effect of sulforaphane on activation of NF-κB. This protective effect of sulforaphane against ROS generation stimulated by LPS has been previously observed in macrophages, and is here shown to be clearly dependent on NF-κB. Once more, it is shown that exemestane and sulforaphane have different modes of action on inflammation. Here exemestane has activity only as a synergist of sulphorophane To evaluate whether the above effect of exemestane depends on aromatase inhibition, letrozole was tested in the same system. Letrozole had no effect on LPS-activated NF-κB by itself, and did not enhance the inhibitory effect of sulforaphane on NF-κB activation, which suggests that this activity of exemestane is not aromatase pathway related.

Example 9

Figure 9A:
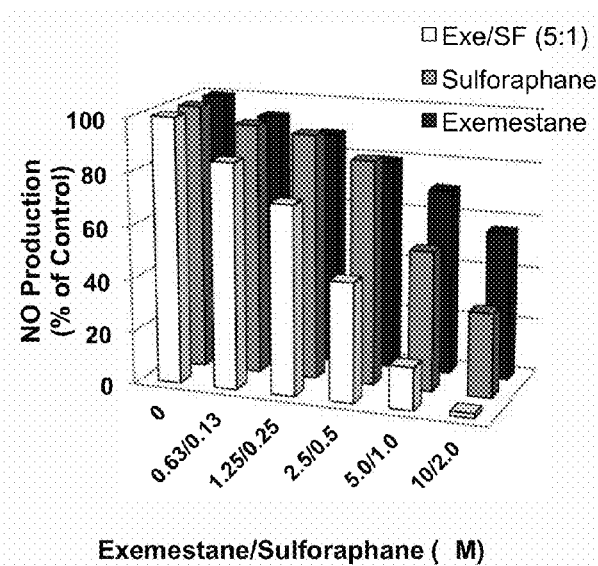
FIGS. 9A-9B depict the synergistic effect of exemestane and sulforaphane on LPS-activated iNOS activity in mouse peritoneal macrophages. Peritoneal macrophages isolated from C57BL6 mice were plated in 96-well plates. Cells were exposed to exemstane, sulforaphane, or their combinations at 5:1 ratio in the presence of 100 ng/ml LPS for 24 hours. NO production was measured as nitrite accumulation in the medium. Control cells were treated with LPS only. Each bar represents the mean of eight replicates (FIG. 9A). CI values from this experiment were obtained by using CompuSyn software. CIs were plotted against the effects (fraction affected) mediated by five different drug combinations (0.75, 1.5, 3.0, 6.0, and 12.0 μM total concentration), respectively (FIG. 9B).
Figure 9B:
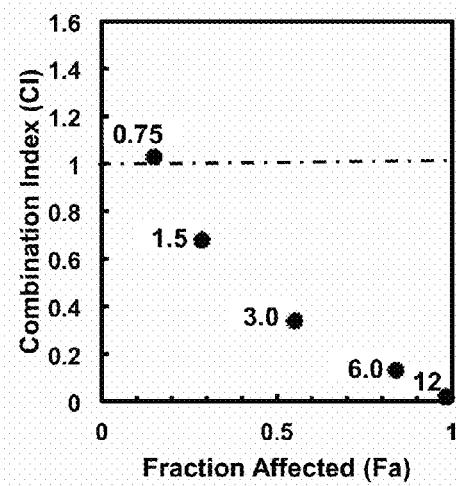

Exemestane and Sulforaphane Synergistically Inhibit LPS-Activated iNOS in Mouse Peritoneal Macrophages Both exemestane and sulforaphane showed dose-dependent inhibitory effects on LPS-stimulated NO production in mouse peritoneal macrophages, and the inhibition by exemestane is more Nrf2-dependent than the inhibition by sulforaphane (FIG. 7B). These results suggest that exemestane and sulforaphane inhibit LPS-activated iNOS in peritoneal macrophages by different molecular pathways targets, and that the combination of the two agents might result in enhanced inhibitory effects. Thus, the inventors determined the inhibitory effects of exemestane, sulforaphane and their combinations (with exemestane and sulforaphane at 5:1 molar ratio) on NO production in LPS-stimulated mouse peritoneal macrophages. As shown in FIG. 9, the combinations of one half-doses of exemestane and of sulforaphane resulted in considerably more potent inhibition on NO production than did the individual treatments with exemestane or sulforaphane at full doses. The mode of interaction between exemestane and sulforaphane in inhibiting iNOS, was further analyzed by the combination dose-response data with the CompuSyn™ program which applies the median effect equation methods. The combined drug effect was expressed as CI (combination index) versus $F_a$ (fraction affected), with CI<1 indicating synergism, CI=1 indicating an additive effect, and CI>1 indicating antagonism. The present experiments established that exemestane and sulforaphane combinations were potently synergistic. Thus, 50% inhibition of LPS-stimulated nitric oxide generation in mouse macrophages required 1.5 µM sulforaphane or 24.2 µM exemestane. A mixture of sulforaphane and exemestane produced the same inhibitory effect at 0.25 µM sulforaphane together with 1.45 µM exemestane, a 5-fold and more than 15-fold reduction in dosage, respectively. This constitutes powerful synergism according to Chou's definitions (Pharmacol Rev 58: 621-681 (2006)) (FIG. 9).

Example 10

Exemestane and Representatives of Other Classes of Compounds which have Phase 2 Enzyme Inducing Capability Synergistically Inhibit LPS-Activated iNOS in Macrophages Since suppression of inflammation has been identified as a consistent feature of many inducers of the phase 2 response, combinations of exemestane with other phytochemical agents, that have similar properties as sulforaphane, were examined We compared the inhibitory potencies of exemestane in combination with three structurally unrelated phytochemicals, shikonin, zerumbone, and resveratrol, on NO production in LPS-stimulated RAW264.7 cells. At 90% inhibition of LPS-stimulated NO production, CI values for exemestane/shikonin (10:1), exemestane/zerumbone (2:1) or exemestane/resveratrol (1:1) were 0.55, 0.77, and 0.64, respectively, which are comparable to the CI value of exemestane/sulforaphane (5:1) 0.69 in RAW264.7 cells. A list of all phase 2 enzyme inducers used in these experiments is shown in Table 1. These results indicate that synergism exists between exemestane and a broad range of classes of phase 2 enzyme inducers.

TABLE 1

Combinations of exemestane and various classes of phase 2 enzyme inducers and their effects on NQO1, iNOS and NF-κB reporter assays.

| Combinations | | NQO1 | iNOS | NF-κB reporter |
|---|---|---|---|---|
| Exemestane | Sulforaphane | N | S*** | E |
| Exemestane | PEITC | | S*** | |
| Exemestane | AITC | | S* | |
| Exemestane | Resveratrol | | S*** | |
| Exemestane | Zerumbone | | S** | |
| Exemestane | Tyrosol | | E | |
| Exemestane | Hydroxytyrosol | | S*** | |
| Exemestane | Curcumin | | S*** | |
| Exemestane | 6-Gingerol | | S*** | |
| Exemestane | EGCG | | N | |
| Exemestane | Capsaicin | | S*** | |
| Exemestane | Genistein | | S*** | |
| Exemestane | HBB2 | | S*** | |
| Exemestane | HBB4 | | S*** | |
| Exemestane | Shikonin | | S*** | |
| Exemestane | Cyclo-shikonin | | S*** | |
| Exemestane | Deoxyshikonin | | S* | |
| Exemestane | Juglone | | E | |
| Exemestane | Plumbagin | | S*** | |
| Exemestane | Menadione | | S** | |

S: synergistic; N: not synergistic;
E: the particular compound had no activity in the specific assay, but it could enhance the activity of exemestane.
PEITC: phenethyl isothiocyanate,
AITC: allyl isothiocyanate,
HBB2: Bis(2-hydroxybenzylidene)acetone,
HBB4: Bis(4- hydroxybenzylidene)acetone.

Combinations of these agents provide a valuable and well-tolerated strategy for prevention, avoiding recurrence, and even treatment of malignancies and other chronic diseases.

The steroid exemestane inhibits the final and rate-limiting step of estrogen biosynthesis, restricts the growth of estrogen-receptor positive mammary cells, and reduces the risk of the recurrence of mammary cancer. Exemestane is highly effective in inhibiting estrogen biosynthesis, as is well illustrated in peripheral fat, which is the principal site of estrogen biosynthesis in postmenopausal women. Quite unexpectedly, the present inventors now show that exemestane exerts a wide range of other, seemingly unrelated biological effects, among which the upregulation of the Keap1-Nrf2-ARE cytoprotective signaling system is probably the most prominent. Thus, in several cell lines (murine hepatoma Hepa1c1c7, murine 308 keratinocytes, adult human retinal pigment epithelial cells [ARPE-19], and rat myocardiocytes [H9c2]) NQO1 is upregulated by exemestane. Furthermore, exemestane protects retinal pigment epithelial cells, myocardiocytes, and keratinocytes against chemically-generated oxidative toxicity resulting from exposure to tert-butyl hyroperoxide and 4-hydroxynonenal, against free radical damage arising from hypoxia-reoxygenation, and from Type A ultraviolet light. Exemestane inhibits LPS-stimulated iNOS activity in macrophages and in monocytes containing multiple NF-κB DNA-binding sequences. But most remarkable is that these protective activities of exemestane, which resemble those of sulforaphane, are modulated in a highly synergistic manner when both exemestane and other phase 2 enzyme inducers, such as sulforaphane, are administered simultaneously.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A composition consisting of an effective amount of exemestane thereof and an effective amount of at least one phase 2 gene inducer, wherein the at least one phase 2 gene inducer is selected from the group consisting of shikonin, zerumbone, reservatrol, phenethyl isothiocyanate (PEITC), allyl isothiocyanate (AITC), hydroxytyrosol, curcumin, 6-gingerol, capsaicin, Bis(2-hydroxybenzylidene)acetone (HBB2), Bis(4-hydroxybenzylidene)acetone (HBB4), cyclo-shikonin, deoxyshikonin, plumbagin, and menadione.

2. A composition consisting of an effective amount of exemestane, a pharmaceutically acceptable carrier and an effective amount of at least one phase 2 gene inducer, wherein the at least one phase 2 gene inducer is selected from the group consisting of shikonin, zerumbone, reservatrol, phenethyl isothiocvanate (PEITC), allvl isothiocyanate (AITC), hydroxytyrosol, curcumin, 6-gingerol, capsaicin, Bis(2-hydroxybenzylidene)acetone (HBB2), Bis(4-hydroxybenzylidene)acetone (HBB4), cyclo-shikonin, deoxyshikonin, plumbagin, and menadione.

3. A composition consisting of an effective amount of exemestane, an effective amount of one or more biologically active agents, a pharmaceutically acceptable carrier and an effective amount of at least one phase 2 gene inducer, wherein the at least one phase 2 gene inducer is selected from the group consisting of shikonin, zerumbone, reservatrol, phenethyl isothiocyanate (PEITC), allyl isothiocyanate (AITC), hydroxytyrosol, curcumin, 6-gingerol, capsaicin, Bis(2-hydroxvbenzvlidene)acetone (HBB2), Bis(4-hydroxybenzvlidene)acetone (HBB4), cyclo-shikonin, deoxyshikonin, plumbagin, and menadione.

* * * * *